United States Patent
Guarracino et al.

[11] Patent Number: 6,096,299
[45] Date of Patent: Aug. 1, 2000

[54] ODOR CONTROL MATERIAL

[75] Inventors: Mario Guarracino, Silivi; Giovanni Carlucci, Chieti; Achille Di Cintio, Pescara, all of Italy

[73] Assignee: The Procter & Gamble Company, Cincinnati, Ohio

[21] Appl. No.: 08/718,363

[22] PCT Filed: Mar. 23, 1995

[86] PCT No.: PCT/EP95/01103

§ 371 Date: Jun. 19, 1997

§ 102(e) Date: Jun. 19, 1997

[87] PCT Pub. No.: WO95/26207

PCT Pub. Date: Oct. 5, 1995

[30] Foreign Application Priority Data

Feb. 23, 1995 [IT] Italy ................................ TO94A0227

[51] Int. Cl.⁷ ............................................. A61L 9/01
[52] U.S. Cl. ...................... 424/76.1; 424/76.8; 424/76.9; 424/402; 424/404
[58] Field of Search ................. 424/76.1, 76.8, 424/76.9, 402, 404

[56] References Cited

U.S. PATENT DOCUMENTS

| | | | |
|---|---|---|---|
| 4,304,675 | 12/1981 | Corey et al. ............................ | 252/8.6 |
| 4,324,246 | 4/1982 | Mullane et al. ........................ | 128/287 |
| 4,341,217 | 7/1982 | Ferguson et al. .................. | 128/290 W |
| 4,342,314 | 8/1982 | Radel et al. ........................... | 128/287 |
| 4,463,045 | 7/1984 | Ahr et al. ............................... | 428/131 |
| 4,525,410 | 6/1985 | Hagiwara et al. ..................... | 428/198 |
| 4,795,482 | 1/1989 | Gioffre et al. ............................ | 55/75 |
| 4,826,497 | 5/1989 | Marcus et al. .......................... | 604/359 |
| 5,306,487 | 4/1994 | Karapasha et al. .................... | 424/76.6 |
| 5,733,272 | 3/1998 | Brunner et al. ........................ | 604/359 |

FOREIGN PATENT DOCUMENTS

| | | | |
|---|---|---|---|
| 0 207 904 | 1/1987 | European Pat. Off. ........ | A61F 13/18 |
| 81/01643 | 6/1981 | WIPO ............................. | A41B 13/02 |
| 91/11977 | 8/1991 | WIPO ............................. | A61F 13/15 |
| 91/12030 | 8/1991 | WIPO ............................. | A61L 9/01 |
| 93/09744 | 5/1993 | WIPO ............................. | A61F 13/15 |
| 94/01069 | 1/1994 | WIPO ............................. | A61F 13/15 |
| 95/17868 | 7/1995 | WIPO ............................. | A61F 13/15 |

*Primary Examiner*—José G. Dees
*Assistant Examiner*—Kathryne E. Shelborne
*Attorney, Agent, or Firm*—Caroline Wei-Berk; Edward J. Milbrada; Mary Catherine Hentz

[57] ABSTRACT

An absorbent article is disclosed for absorbing bodily fluids which has incorporated therein an odor control material for decreasing bodily odor which material comprises a zeolite having an average particle size (distribution by weight in sieve analysis) of at least 200 um. The zeolite may optionally be mixed with an absorbent gelling material and/or activated carbon.

12 Claims, 4 Drawing Sheets

ODOR CONTROL MATERIAL

FIELD OF INVENTION

This invention relates to an odour control material, and in particular to an absorbent article for absorbing bodily fluids comprising the odour control material and to the use of a zeolite as an odour control material.

BACKGROUND OF THE INVENTION

Absorbent articles are designed to be worn by humans to absorb bodily fluids, such as urine, menstrual fluid and perspiration, etc. Examples of absorbent articles include sanitary napkins, pantiliners, disposable diapers, incontinence pads, tampons and the like.

In use, the absorbent articles are known to acquire a variety of compounds, for example volatile fatty acids (e.g. isovaleric acid), ammonia, amines (e.g. triethylamine), sulphur containing compounds (e.g. mercaptans, sulphides), alcohols, ketones and aldehydes (e.g. furaldehyde) which release unpleasant odours. These compounds may be present in the bodily fluid or may be produced by fermentation once the bodily fluid is absorbed into the pad. In addition bodily fluids can contain microorganisms that can also generate malodorous by products. Unpleasant odours which emanate from absorbent pads when in use may make the wearer feel self conscious.

Various odour controlling materials have been disclosed. In particular, certain zeolitic materials are becoming known for their odour controlling properties. Zeolitic materials are generally quite safe and have been found to control many odours associated with bodily fluids.

Zeolites as odour controlling materials have been disclosed in the art, as is discussed below.

U.S. Pat. No. 4,304,675 discloses a powdered carpet treatment composition containing a natural or synthetic zeolite, which zeolite is preferably zeolite A. The zeolite is said to have a particle size of 3.5 $\mu$m and in which about 4% of the particles have a micrometer size of greater than 10 micrometers.

U.S. Pat. No. 4,525,410 discloses a fibre article having antibacterial properties comprising zeolitic particles retaining therein at least one metal ion having bactericidal property and a mixed fibre assembly. The zeolite has a low framework ratio of $SiO_2/Al_2O_3$. The zeolite has the ions $Ag^+$, $Cu^{2+}$ or $Zn^{2+}$ associated therewith.

WO 81/01643 discloses the removal of ammonia (and other toxic or potentially toxic nitrogenous irritants) from diapers by incorporating into the diaper an inorganic aluminosilicate zeolite ammonium ion exchange material. The zeolite is said to be synthetic or natural and the only zeolite exemplified is naturally occurring clinophlolite.

U.S. Pat. No. 4,826,497 discloses fibrous absorbent articles intended for the absorption of bodily fluids comprising synthetic zeolites prepared using an organic templating agent prepared in siliceous form in which at least about 90% of the framework tetrahedral units are $SiO_2$ tetrahedra, which has pore diameters of at least 5.5 Å and has a capacity for absorbed water of not greater than 10% under standard conditions. The framework ratio of $SiO_2/Al_2O_3$ of the synthetic zeolite is high. The Examples all utilize steam treated zeolite Y or silicalite.

WO 91/11977 discloses a method for decreasing odours associated with bodily fluids comprising contacting said fluids with an odour controlling amount of an intermediate framework $SiO_2/AlO_2$ zeolite.

In the prior art disclosures all the zeolite odour controlling materials tend to be in the form of very small dusty particles which are difficult to handle on a commercial scale; they generally have a size of <5 $\mu$m. Such materials tend to be blown or vacuumed up from absorbent structures moving at high speeds (500–600 items/minute) used on modern catamenial or diaper manufacturing lines and this is a problem.

A system has been suggested to overcome this problem and in particular WO 91/12030 discloses combining particulate carbon odour controlling agents with white coloured zeolite or other "masking materials", using binder materials. This system is however expensive and the effectiveness of the odour control material can be reduced.

The object of the present invention is thus to provide an absorbent article providing odour control using an material which can be handled easily in production of an absorbent article, which has good odour controlling properties and is not expensive.

SUMMARY OF THE INVENTION

It has been surprisingly found that zeolites in a form having an average particle size (distribution by weight in sieve analysis) of at least 200 $\mu$m act as a very efficient odour control material and can be easily handled.

Accordingly the present invention provides an absorbent article having incorporated therein an odour control material for decreasing odours associated with bodily fluids which material comprises a zeolite having an average particle size (distribution by weight in sieve analysis) of at least 200 $\mu$m.

The present invention also provides an odour control composition for decreasing bodily odour associated with bodily fluids which composition comprises a zeolite having an average particle size (distribution by weight in sieve analysis as hereinbefore defined) of at least 200 $\mu$m together with an absorbent gelling material (AGM) and/or activated carbon.

Preferably the average particle size of the zeolite is from 200 to 500 $\mu$m, more preferably from 300 $\mu$m to 400 $\mu$m.

BRIEF DESCRIPTION OF THE DRAWINGS

The invention will now be illustrated with reference to the detailed description and examples taken in conjunction with the accompanying Figures.

DETAILED DESCRIPTION OF THE INVENTION

Figure 1:
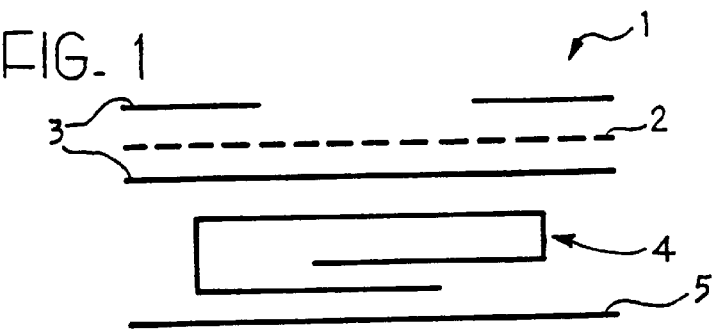
FIG. 1 shows a cross sectional view of a commercially available pantiliner is namely the Always Comfort Pantiliner by Procter & Gamble Company.

The sieve analysis method as mentioned above is performed as follows:

The particle size distribution and the average particle size of a material (zeolites, activated carbon, AGM etc.) is determined by a mechanical sieve shaker method using an electromagnetic sieve shaker Fritsch ® Analysette 3 with six analytical sieves (20, 30, 40, 70, 100 and 140 Mesh, respectively corresponding to 850, 600, 425, 212, 150 and 106 μm) and one sieve pan. The selected sieves are nested with the coarsest sieve at the top and the solid pan at the bottom, then the test sample (100 g of material) is placed on the top sieve and the nest is closed with a cover. The shaker is operated for 15 minutes continuously with an amplitude of vibrations of 1 mm and finally, after the completion of the agitation, the material retained on each sieve is weighed separately. The material which has passed through the finest sieve into the pan is also weighed.

These weights and the weight of the original test sample are used to calculate the particle size distribution and the average particle size of the test sample. The particle size distribution is obtained by simply dividing the weight of the material retained on each sieve by the total weight of the test sample. In order to get the average particle size the percentage retained on each sieve is calculated by dividing the "total weight coarser" than that sieve by the total weight of the test sample. The total weight coarser includes the material retained on that particular sieve plus all material on all coarser sieves. This cumulative percentage represents the total percentage of the test sample coarser than the aperture of that particular sieve.

The data is plotted on a sieve analysis graph where the abscissa represents the sieve sizes (on a logarithmic scale) and the ordinate the percentages retained (on a linear scale). By interpolation on the sieve analysis graph the sieve size corresponding to a percentage of 50% retained can be evaluated, and this size is taken as the average particle size of the sample.

The zeolite may be used as such or in a form which has been granulated with a binder.

The zeolite used in the present invention is a known material. While some naturally occurring zeolites meet the objectives of the invention synthetic zeolites of the types available in commerce are generally preferred.

In general terms, zeolites comprise an aluminate/silicate framework, with associated cations, M, providing overall electrical neutrality. Empirically, the zeolite framework can be represent as

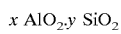
$$x\, AlO_2.y\, SiO_2$$

and the electrical neutral zeolite as

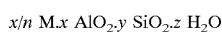
$$x/n\, M.x\, AlO_2.y\, SiO_2.z\, H_2O$$

wherein: x and y are each integers, M is a cation and n is the charge on the cation. As noted by the empirical formula, zeolites may also comprise water of hydration (z $H_2O$). Reference to the literature will illustrate that M can be a wide variety of cations, e.g. $Na^+$, $K^+$, $NH_4^+$, alkylammonium, heavy metals and the like. The practice of the present invention does not require any particular selection of cation; accordingly the sodium ion is convenient and preferred.

The manufacture of zeolite materials of the type used in the practice of this invention is well-known, and reference can be made to the literature for typical synthetic procedures. For example attention is directed to synthetic procedures described in the following reference texts: ZEOLITE SYNTHESIS, ACS Symposium Series 398, Eds. M. L. Occelli and H. E. Robson (1989) pages 2–7; ZEOLITE MOLECULAR SIEVES, Structure, Chemistry and Use, by D. W. Breck, John Wiley & Sons (1974) pages 245–250, 313–314 and 348–352; MODERN APPLICATIONS OF MOLECULAR SIEVE ZEOLITES, Ph.D. Dissertation of S. M. Kuznicki, U. of Utah (1980), available from University Microfilms International, Ann Arbor, Michigan, pages 2–8.

The zeolite used in the present invention preferably has less than 10%, preferably less than 7% by weight of particles having a size less than 100 μm.

The zeolite preferably has a low framework ratio, in particular it has a framework ratio of $SiO_2/Al_2O_3$ of not more than 4:1, preferably not more than 2:1.

The zeolite preferably has a pore diameter of from 0.30 to 0.55 nm, preferably from 0.4 to 0.45 nm.

The zeolite is preferably a zeolite A and more preferably a $Na^+$ zeolite A.

The zeolite preferably is a compound based on a zeolite A which is granulated with sodium sulphate and carboxy methyl cellulose (CMC). This zeolite is sold by Degussa AG under the trade name Wessalith CS. The zeolite may also be granulated with bentonite and/or polyacrylate and is sold under the trade name Wessalith by Degussa AG. Although any zeolite having an average particle size of at least 200 μm may be used in the practice of the invention.

The odour control material may also comprise other conventional compounds, for example activated carbon, other zeolites;

charcoal, antimicrobial agents, ionic absorbents, such as an absorbent gelling material (AGM) or known odour control agents in powder form.

It is essential that the conventional compounds are also in powder form which powders conventionally have average particle sizes of at least 200 μm, preferably from 200 to 500 μm thus enabling the odour control material to be easily handled and dosed with the conventional compound.

Preferably the odour control material also comprises AGM or activated carbon, more preferably it comprises AGM and activated carbon. The material may also comprise AGM and bentonite. The AGM, activated carbon and bentonite all have odour controlling properties. The quantity of AGM, activated carbon and bentonite used with the odour control material may readily be determined by the skilled person dependant on the absorbent article in question.

It has been found that from 2 to 70% of the total weight of the absorbent article should be made up of the odour control material, which material may be zeolite alone or zeolite together with AGM and/or activated carbon. For products having a weight of approximately 2 g a preferred quantity of odour control material is 0.7 g which quantity provides odour control. For 0.7 g of odour control material it is preferable to have about 31% by weight of zeolite, AGM and about 26% by weight activated carbon. Another preferred odour control material has 0.4 g zeolite and 0.3 g (about 43% by weight) absorbent gelling material.

The absorbent article may be a sanitary napkin, a pantiliner, a disposable diaper, an incontinence pad, tampon or the like. According to one aspect of the invention the absorbent article is a pantiliner. According to another aspect of the invention the absorbent article is a sanitary napkin.

The weight of the odour control material which may be used in the absorbent article can be readily determined by the skilled person bearing in mind the size of the absorbent article in question. For example a suitable quantity of odour control material which may be used in a pantiliner is from 0.05 to 0.8 g, preferably the quantity is from 0.1 to 0.5 g.

Preferably AGM is included in the article together with the odour control material used in the present invention. The quantity of AGM which may be added may be readily determined by the skilled person for each absorbent article. Preferably 0.05 to 0.7 g and more preferably from 0.1 to 0.5 g of AGM is added to a pantiliner.

The odour control material may be incorporated into the article by methods known in the art, for example layered on or into the core of the absorbent material or mixed within the fibres of the absorbent core. The odour control material is preferably incorporated between two layers of cellulose tissue, optionally the material may be bonded between two cellulose tissue layers with, for example, a hot melt adhesive or any suitable bonding system.

More preferably AGM and activated carbon are included in the article together with the odour control material used in the present invention. The AGM is included in the amounts shown above and the activated carbon is included in amounts of from 0.05 to 0.7 g, more preferably from 0.1 to 0.5 g in the pantiliner.

More preferably the odour control material is incorporated in a layered structure in accordance with the disclosure of WO 94/01069 or TO 93A 001028. TO 93A 001028 describes a layered structure substantially as described in WO 94/01069 with the exception that TO 93A 001028 comprises a much higher quantity of AGM in the intermediate layer which is between the fibrous layers, namely in an amount exceeding 120 g/m$^2$. In addition the intermediate layer in TO 93A 001028 also comprises thermoplastic material, which when heated, melts and bonds the first and second layers together with the intermediate layers and thus AGM between them. The bridges which form the bond points between the fibrous layers involve particles of AGM as well as particles of thermoplastic material. The absorbent capacity of the AGM is unaffected by bonding.

An absorbent article, namely a pantiliner which is an exemplary embodiment of an article into which the odour control material may be incorporated, is shown in cross section in FIGS. 1 to 4.

The pantiliner may be of any shape known in the art, for example, rectangular, hour glass, winged, etc.

Figure 2:
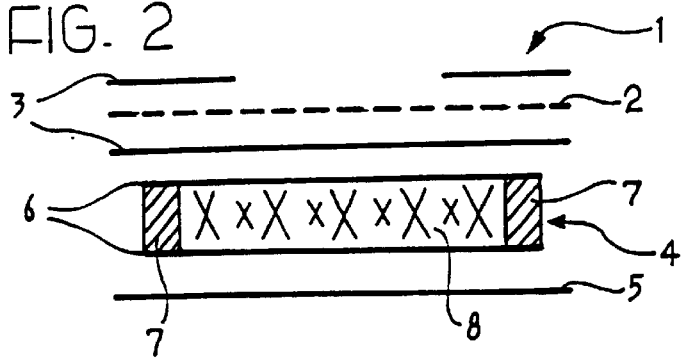
FIG. 2 shows a cross sectional view of a pantiliner having the odour control material incorporated therein.

As shown in FIGS. 1 and 2 pantiliner 1 comprises a liquid pervious topsheet 2, a secondary top sheet 3, an absorbent core 4 and a liquid impervious backsheet 5. It is not, however, intended that the pantiliner should be limited to embodiments comprising all such elements. Additional elements known to the skilled person may also be included in the pantiliner.

The topsheets 2 and 3 are liquid permeable and, when pantiliner 1 is in use, are in close proximity to the skin of the user. The topsheet 2 and 3 are compliant, soft feeling and non-irritating to the user's skin. It can be made from any of the conventional materials for this type of use. Non-limiting examples of suitable materials that can be utilized as the topsheets 2 and 3 are woven and non-woven polyester, polypropylene, nylon and rayon and formed thermoplastic films. Formed films are preferred for topsheet 2. Suitable formed films are described in U.S. Pat. No. 4,324,246, U.S. Pat. No. 4,342,314, U.S. Pat. No. 4,341,217 and U.S. Pat. No. 4,463,045. Secondary topsheet 3 is preferably a non-woven, more preferably an air through non-woven with a basis weight of 21 g/m$^2$, the non-woven being as disclosed in WO 93/09744.

The formed films are preferred for topsheet 2 because they are pervious to liquids and yet non-absorbent. Thus, the surface of the formed film, which is in contact with the body, remains dry and is more comfortable to the wearer. The topsheet may be constituted by the covering structure for sanitary products described in EP-A-0 207 904. Preferably the topsheet 2 is made of polyethylene perforated film (24.5 g/m$^2$).

The inner surface of secondary topsheet 3 may be secured in contacting relation to absorbent core 4. This contacting relationship results in liquid penetrating the topsheet 3 faster than if it were not in contact with absorbent core 4. Topsheet 3 can be maintained in contact with the absorbent core 4 by applying adhesive, preferably in spaced limited areas. Examples of suitable adhesives used for such purpose include the acrylic emulsion E-1833BT manufactured by the Rohm & Haas Company, Philadelphia, Pa. and the acrylic emulsion WB 3805 manufactured by H. B. Fuller Company of St. Paul, Minn. The adhesives can be applied by any of the common techniques well known to those skilled in the art, for example, the adhesive may be applied by spraying, by padding or by the use of transfer rolls. The adhesive may be in the form of a uniform continuous layer, a patterned layer of adhesive, or an array of separate lines, spirals or spots of adhesive. The absorbent core 4 is preferably secured in contacting relation to the secondary topsheet 3.

Referring again to FIGS. 1 and 2, it can be seen that absorbent core 4 is positioned between secondary topsheet 3 and backsheet 5. Absorbent core 4 provides the absorptive means for absorbing the bodily fluid. Absorbent core 4 is generally compressible, conformable and non-irritating to the user's skin. It can comprise any material used in the art for such purpose. Examples of such materials include multiple plies of creped cellulose wadding, fluffed cellulose fibres, wood pulp fibres also known as airfelt, textile fibres, a blend of fibres, a mass or batt of fibres, a web of polymeric fibres, a blend of polyester and polypropylene fibres, layers of cellulose tissue or layers of air laid tissue.

Preferably, the core comprises a mass or batt of fibres. While many types of fibres may be used, a preferred material is a batt of polyester fibres. More preferably the core comprises cellulose tissue (63 g/m$^2$) which forms a plurality of absorbent layers. FIG. 1 shows an absorbent core 4 formed by one layer of cellulose tissue which has been folded as shown. FIG. 2 shows an absorbent core comprised of two layers of air laid cellulose tissue 6 joined at their longitudinal edges with adhesive 7.

Figure 3:
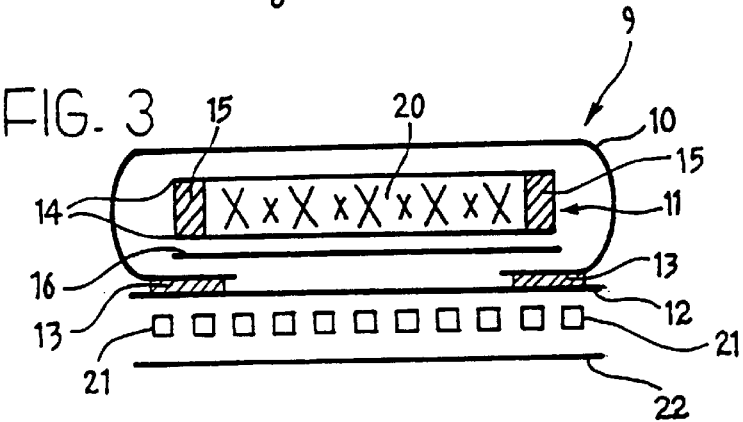
FIG. 3 shows a cross sectional view of a pantiliner having an absorbent core comprising three cellulose tissue layers, the odour control material being incorporated between the first and second tissue layers.
Figure 4:
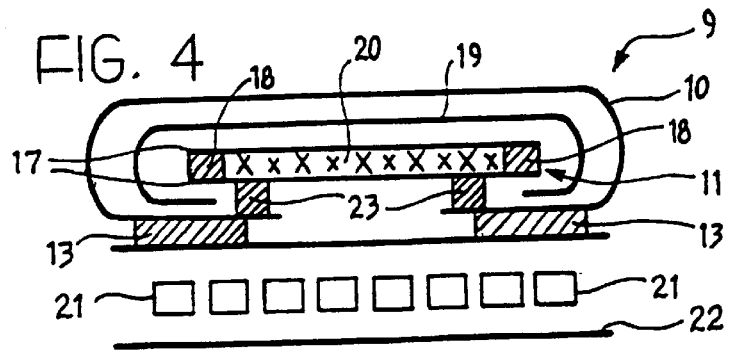
FIG. 4 shows a cross sectional view of a pantiliner having an absorbent core comprising three cellulose tissue layers, the odour control material being incorporated between the second and third tissue layers.

Preferably, the odour control material disclosed herewith is incorporated into the absorbent core by known techniques. It may, for example, be layered on or into the absorbent core or mixed with the fibres of the core. More preferably the odour control material 8, 20 is layered in accordance with the teaching of WO 94/01069 or TO 93A 001028 as discussed previously between two layers of air laid cellulose tissue and the laminate is as shown in FIGS. 2 to 4 above. In particular polyethylene powder, as thermoplastic material, is mixed with the odour control material of the present invention, preferably zeolite, AGM and activated carbon, the mixture is heated such that the polyethylene melts and glues the laminate layers and components together. Adhesive lines are preferably also placed on the edges of the laminate as shown as 7, 15 and 18 in the Figures to ensure that edges of the laminate stick together and any loose odour control material does not fall out of the laminate.

As shown in FIGS. 3 and 4, pantiliner 9 comprises a liquid pervious topsheet 10, an absorbent core 11, a liquid impervious backsheet 12, adhesive 13 which fastens the topsheet 10 to the backsheet 12, a layer of adhesive 21 which is secured to the backsheet 12 and which is covered by removable release liner 22. The removable release liner 22 and associated adhesive 21 may also be included in the pantiliners of FIGS. 1 and 2. In FIG. 4 adhesive 23 in addition fastens the absorbent core 11 to the portions of the topsheet 10 folded under the core 11. It is not, however, intended that the pantiliner should be limited to embodiments comprising all such elements. Additional elements known to the skilled person may also be included in the pantiliner.

Topsheet 10 is liquid permeable and, when pantiliner 9 is in use, is in close proximity to the skin of the user. The topsheet 10 is as described for topsheet 2 in FIGS. 1 and 2.

The inner surface of topsheet 10 may be secured in contacting relation to absorbent core 11 as described for the pantiliner of FIGS. 1 and 2.

Preferably the topsheet 10 wraps around the core 11, as shown in FIGS. 3 and 4, and is fastened by means of an adhesive 13 to backsheet 12.

Referring again to FIGS. 3 and 4, it can be seen that absorbent core 11 is positioned between topsheet 10 and backsheet 12. Absorbent core 11 is as described for FIG. 2. FIG. 3 shows an absorbent core comprised of two layers of air laid cellulose tissue 14 joined at their longitudinal edges with adhesive 15 and having a layer of cellulose tissue 16 there beneath to form a three layered absorbent core. FIG. 4 shows two layers of air laid tissue 17 joined at their longitudinal edges with adhesive 18 and having a layer of cellulose tissue 19 wrapped there around to form the third layer of the absorbent core.

Referring to FIGS. 1 to 4, the pantiliner is provided with a backsheet 5, 12 which backsheet is impervious to liquids and, thus, prevents body fluid which may be expressed from absorbent core 4, 11 from soiling the body or clothing of the user. Suitable materials are well known in the art, including woven and non-woven fabrics which have been treated to render them liquid repellent. Breathable or vapour pervious, liquid resistant materials, and those materials described in U.S. Pat. No. 3,881,489 and U.S. Pat. No. 398,986 can also be used. Preferred materials are those materials that are fluid and vapour impervious, because they provide additional fluid strikethrough protection. Especially preferred materials include formed thermoplastic films. One especially cuitable material is a polyethylene film having a thickness of from about 0.075 mils to about 1.25 mils, with a 1.0 mil thickness polyethylene film being especially suitable. Preferably the backsheet 5, 12 is polyethylene embossed film (24.4 g/m$^2$).

The outer surface of backsheet 5, 12 may be coated with adhesive 21. Adhesive 21 provides a means for securing the pantiliner in the crotch portion of a panty. Any adhesive or glue used in the art for such purpose can be used herein, with pressure sensitive adhesives being preferred. Suitable adhesives are Century A-305-IV manufactured by the Century Adhesives Corporation and Instant Lok 34-2823 manufactured by the National Starch Company. Also, before pantiliner 1 or 9 is placed in use, the pressure sensitive adhesive 21 should be covered with removable release liner 22 in order to keep adhesive 11 from drying out or sticking to a surface other than the crotch portion of the panty prior to use. Any commercially available release liners commonly used for such purposes can be utilized herein. Non-limiting examples of suitable release liners are BL 30 MG-A Silox El/O and BL 30 MG-A Silox 4 P/O both of which are manufactured by the Akrosil Corporation. Preferably the release liner is a silicon paper having a thickness of about 45 $\mu$m (43.5 g/m$^2$). Other means which are known in the art may be used to affix the pantiliner in the crotch portion of a panty. FIGS. 3 and 4 show an embodiment which comprises the adhesive 21 and removable release liner 22.

The backsheet 5, 12 is preferably secured in the absorbent core 4, 11 by securement means (not shown), such as those well known in the art.

The invention will now be illustrated with reference to the examples wherein the article for absorbing bodily fluids is a pantiliner or a sanitary napkin. It will, of course, be appreciated that other absorbent articles may also have the odour control material incorporated therein, the incorporation of the odour control material into the pant liner may be achieved by other known methods and the odour control material may be any of those disclosed in the present specification.

EXAMPLES

Incorporation of the Odour Control Material into a Pantiliner

The pantiliners used in the following examples were Always COMFORT Pantiliners (Always is a Registered Trade Mark) as sold by the Procter & Gamble Company. Each pantiliner was opened at one end. The cellulose tissue sheet, which constitutes the absorbent core of the product was substituted with two layers of cellulose tissue that incorporate the odour control material homogeneously dispersed therein as shown in FIG. 2. The whole pantiliner structure was then reconstituted.

Samples were prepared by the method as described above, which samples incorporate the odour control material (OCM) as described herein together with AGM, AGM and activated carbon as illustrated in Table 1 below wherein the total quantity of material, in grams, incorporated into each sample is shown.

The Odour Control Material used in the samples is the zeolite Wessalith CS available from Degussa AG.

The AGM used in the samples is Drytech XZ 95890.01, available from Dow Europe and the activated carbon is PCB type available from Calgon Company Corporation (USA).

A commercially available Always Comfort (Always is a Registered Trade Mark) pantiliner without modification was used as a reference (Blank sample 0).

TABLE 1

| | Quantity of material in g | | |
|---|---|---|---|
| Sample | OCM (zeolite) | AGM | Activated carbon |
| 1 | 0.40 | 0.30 | — |
| 2 | 0.22 | 0.30 | 0.18 |

Odour Control Test Protocol

Each test comprises four separate stages which may be summarised as follows:

a) Consignment of the products.

b) Product return and preparation of the test samples.

c) Sniff-test.

d) Statistical analysis of the Data.

Each stage is described in more detail below.

a) Women were chosen who were known to have an odour control problem. Each of five women selected were given one product per test sample individually packaged in an anonymous bag. Every product was worn for seven hours.

b) The used product was placed into an aluminum tray, approximately 1 cm deep, covered with a perforated aluminum sheet, in order to keep it out of view, and finally covered with another tray of the same type, which was kept thereon in inverted position up to the moment of the sniff-test.

c) The sniff-test was performed in a pre-ventilated room by five graders. Each grader had been preselected for their sensitivity to the unpleasant smells present in an absorbent article after use and their ability to grade the unpleasantness of the odour in a consistent manner. Every grader evaluated the odour of each series of five products representing each sample using a pleasantness scale which ranges from −10 (highest level of unpleasantness) to 5 (most pleasant). The pleasantness values for each sample were obtained as a mean of 25 observations (five grades, five products for each sample).

d) The results collected from the test were then analyzed by statistical analysis software (SAS). The data was processed in order to show statistically significant differences between the treated and untreated products.

This difference is shown in the tables by means of a letter (in the "Significant difference" column) near every mean value; results with the same letter are not statistically significantly different.

Duncan's Multiple Range Test was used to form Multiple comparisons. Values of $p<0.05$ were considered statistically significant.

Example 1

Sample type 1 was tested together with the reference (blank sample 0).

Figure 5:
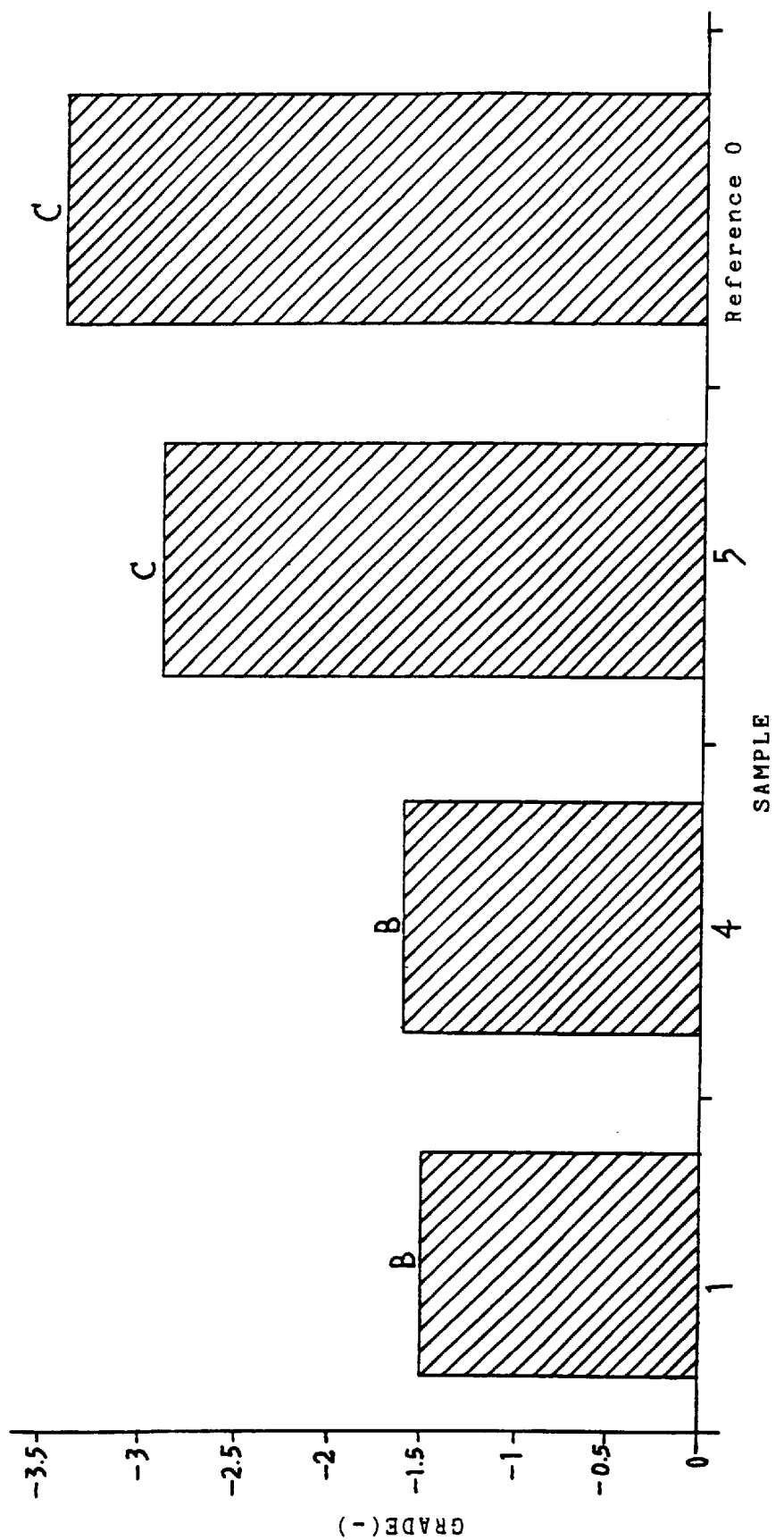
FIG. 5 shows the results of comparative example A.

It can be seen from the results collected in Table 2 and in FIG. 5 that the treated sample was statistically different from the reference and in particular sample 1 having the odour control material as disclosed herein together with AGM, controls the odour when compared to the reference.

TABLE 2

| Sample type | Significant difference |
|---|---|
| 1 | B |
| 0 | C |

Example 2

The sample 2 was tested together with the reference (blank sample 0). It can be seen from Table 3 and FIG. 6 that the odour control material together with AGM and activated carbon (sample 2) controls odour when compared to the blank.

TABLE 3

| Sample type | Significant difference |
|---|---|
| 2 | A |
| 0 | C |

Comparative Example A

Sample 1 from Example 1 was compared to the following samples.
Sample 4
  0.30 g AGM+0.40 g zeolite Abscents
Sample 5
  0.30 g AGM+0.40 g zeolite Y.
The zeolite Abscents is available from UOP (USA) and has a particle size of 5 $\mu$m and is as disclosed in U.S. Pat. No. 4,826,497. The AGM is the same as that mentioned previously. Zeolite Y is CBV 400 Zeolite HY available from PQ Corporation (USA).

The reference sample is as before. The results are shown in Table 4 and in FIG. 5.

TABLE 4

| Sample | Significant difference |
|---|---|
| 1 | B |
| 4 | B |
| 5 | C |
| 0 | C |

In FIG. 5 the scale on the Y axis, namely the unpleasantness grade, is a negative scale showing a maximum unpleasantness of −3.5 for Sample 0.

It can be seen that the odour control material with AGM (sample 1) has the same odour control capacity of Abscents and AGM but is not dusty and is thus much easier to handle than the conventionally used zeolites. In addition the odour control material as disclosed herein is significantly cheaper than the conventionally used Abscents zeolite. The odour control material as disclosed herein with AGM (sample 1) is surprisingly significantly better than a conventionally used zeolite Y.

Comparative Example B

Sample 2 from Example 2 is compared to the following samples.
Sample 6
  0.30 g AGM+0.22 zeolite Y and 0.18 g activated carbon.
Sample 7
  0.30 g AGM+0.45 g agglomerate zeolite Y/activated carbon.
Zeolite Y is the same as that used in comparative Example A. The activated carbon was as mentioned previously. The agglomerate of zeolite Y and activated carbon is as disclosed in WO 91/12030.
The sample reference is as before.
The results are shown in Table 5 and FIG. 6.

TABLE 5

| Sample | Significant difference |
|---|---|
| 2 | A |
| 6 | B |
| 7 | B |
| 0 | C |

Figure 6:
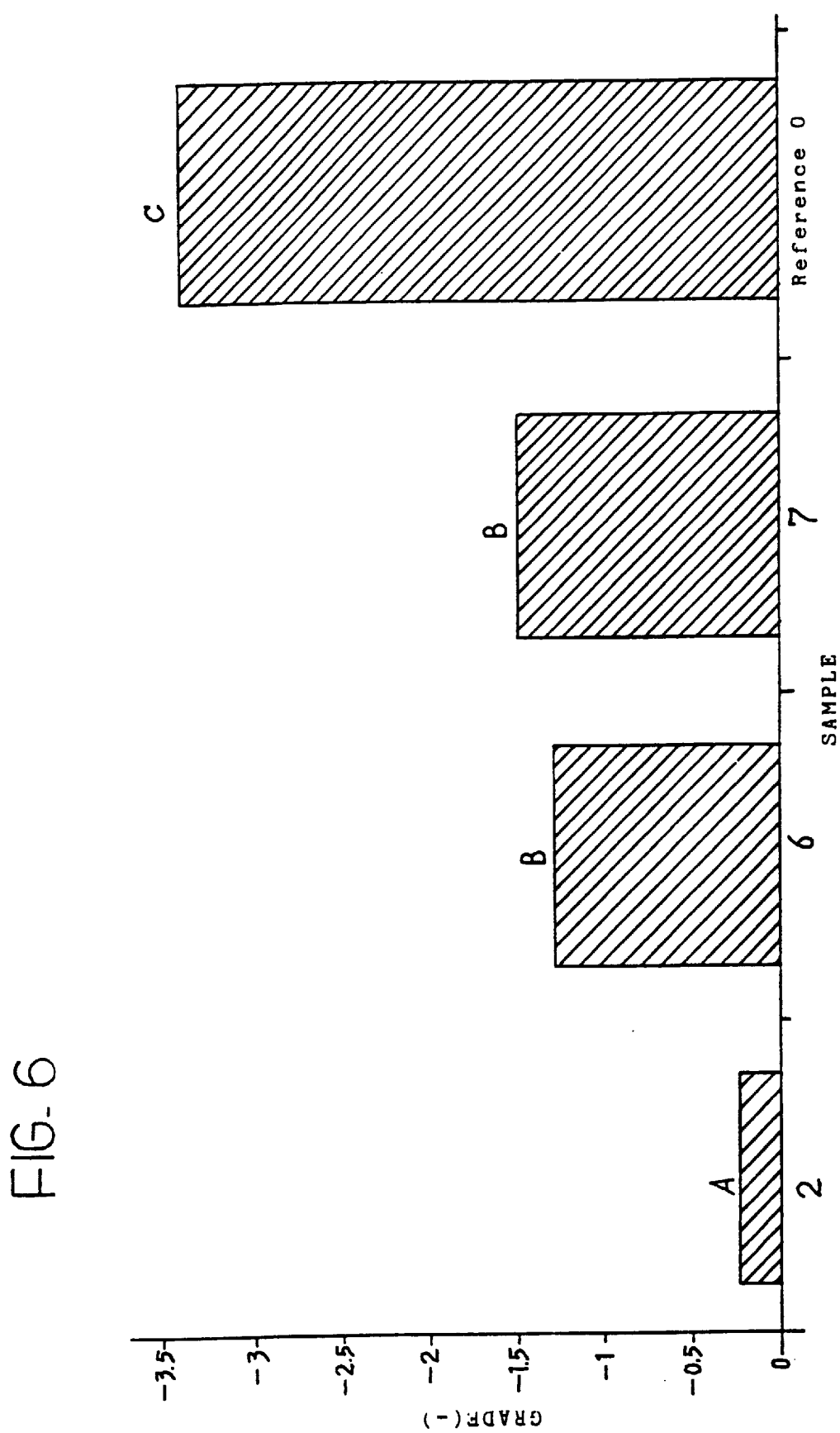
FIG. 6 shows the results of comparative example B.

In FIG. 6 the scale on the Y axis, namely the unpleasantness grade, is a negative scale showing a maximum unpleasantness of −3.5.

It was surprisingly found that the Sample 2, of the present invention, controlled odour significantly better than either Sample 6 or 7.

Similar results were obtained when the odour control material was incorporated into a sanitary napkin in the following manner.

Incorporation of the OCM into a Sanitary Napkin

The samples were obtained from commercially available Lines Liberty Idea sanitary napkins as sold by Fater SpA.

Each napkin is opened by cutting the wrap around perforated coverstock at its bottom face approximately along a longitudinal edge of the release paper which covers the external adhesive layer.

The side of the absorbent fibrous core is then exposed by slightly shifting the water impermeable plastic bottom layer and, subsequently, the fibrous core is split into two halves, each having approximately the same thickness, along a plane which is parallel to the plane of the napkin itself.

The odour control material is homogeneously dispersed between these two fibrous layers which are then joined together to reconstitute the absorbent core.

The water impermeable inner backsheet is then put back into its original position and the wrap around perforated coverstock is sealed along the cut by means of e.g. a double sided adhesive tape.

The test protocol is substantially the same as previously described for the pantiliners, with the exception that the mean values of the unpleasantness obtained from the 25 observations for each sample have been corrected with a statistical technique called "covariance analysis" to take into account the fact that there was not a fixed wearing time for the sanitary napkins.

The results obtained are as follows:

Example 3

Sample type 3 and a reference blank sample 0 were tested in order to show the odour removing capability of the odour control material as disclosed herein.
Sample 3
  0.4 g OCM The pleasantness grade values show statistically significant differences between the product with the odour control material and the reference (blank sample 0) thus showing effective odour control by sample 3.

TABLE 6

| Sample type | Significant difference |
|---|---|
| 3 | D |
| 0 | C |

Comparative Example C

Sample 3 from Example 3 was compared to the following Sample.
Sample 8
  1 g zeolite Abscents (Abscents is a registered trade mark)
  Abscents is available from UOP (USA) has a particle size of 5 $\mu$m and is as disclosed in U.S. Pat. No. 4,826,497.

The reference sample is as before. The results are shown in Table 7 and also in FIG. 7

TABLE 7

| Sample | Significant difference |
|---|---|
| 3 | D |
| 8 | D |
| 0 | C |

Figure 7:
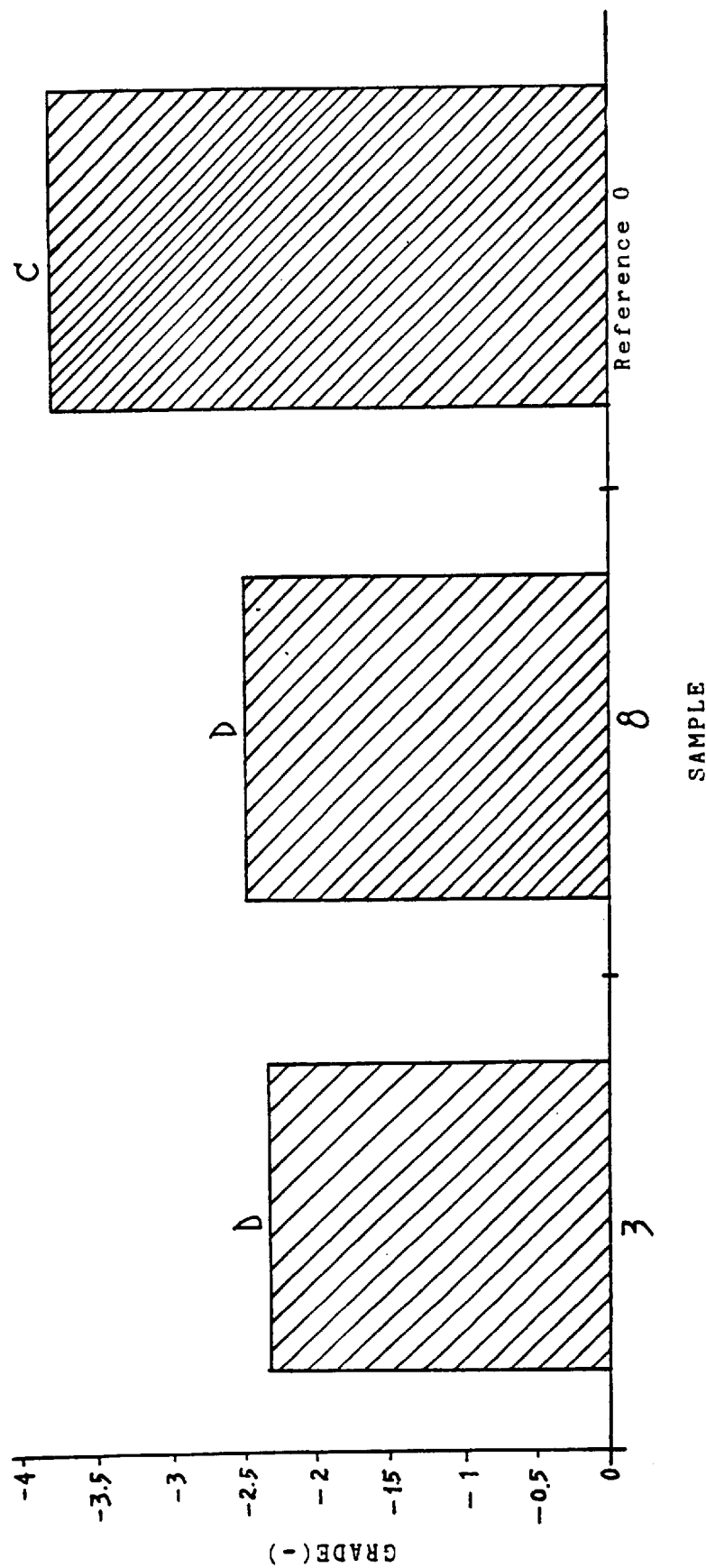
FIG. 7 shows the results of comparative example C.

In FIG. 7 the scale on the Y axis, namely the unpleasantness grade, is a negative scale showing a maximum unpleasantness of −4.

It is shown that the odour control material used in the present invention has the same odour control ability of a conventionally used zeolite however the odour control material used in the present invention is not dusty and is thus much easier to handle than the conventionally used zeolite and is also much cheaper.

A further material which controls odour in accordance with this invention is shown in Example 4.

Example 4

0.15 g OCM(zeolite)+0.20 g AGM+0.12 g activated carbon wherein the zeolite, AGM and activated carbon are those as used for the samples shown in Table 1.

What is claimed is:

1. An absorbent article having an odour control material for decreasing bodily odour associated with bodily fluids, the odour control material consisting of zeolite particles having an average particle size of at least 200 $\mu$m.

2. An absorbent article as claimed in claim 1 wherein the average particle size of the zeolite is from about 200 $\mu$m to about 500 $\mu$m.

3. An absorbent article as claimed in claim 1 wherein less than 10% by weight of the zeolite particles have a particle size less than 100 $\mu$m.

4. An absorbent article as claimed in claim 1 wherein the zeolite has a pore diameter of from about 0.30 nm to about 0.55 nm.

5. An absorbent article as claimed in claim 1 wherein the zeolite is granulated with a binder.

6. An absorbent article as claimed in claim 5 wherein the zeolite is granulated with sodium sulphate and carboxy methyl cellulose.

7. An absorbent article as claimed in claim 1 wherein the zeolite has a framework ratio of silicon dioxide to aluminum oxide of not more than 4:1.

8. An absorbent article as claimed in claim 1 wherein the zeolite is zeolite A.

9. An absorbent article as claimed in claim 1 wherein the zeolite comprises a cation, and the cation is selected from the group consisting of sodium ions, potassium ions, ammonium ions, alkylammonium ions, and heavy metal ions.

10. An absorbent article as claimed in claim 1 wherein the odour control material comprises from about 2 to about 70% of the total weight of the absorbent article.

11. An absorbent article as claimed in claim 9 wherein the cation is a sodium ion.

12. A composition as claimed in claim 11 wherein the cation is a sodium ion.

* * * * *

UNITED STATES PATENT AND TRADEMARK OFFICE
CERTIFICATE OF CORRECTION

PATENT NO.   : 6,096,299
DATED        : August 1, 2000
INVENTOR(S)  : Guarracino et al.

It is certified that error appears in the above-identified patent and that said Letters Patent is hereby corrected as shown below:

Title page,
Item [30], Foreign Application Priority Data, please delete "Feb. 23, 1995" and insert therefor -- March 25, 1994 --. and please delete "TO94A0227" and insert therefor -- TO94A000227 --.
Item [57], ABSTRACT,
Line 5, please delete "um" and insert therefor -- $\mu$m --.

Column 2,
Lines 22-25, after (SUMMARY OF THE INVENTION), please insert the following paragraph:
-- The odour control material has a surprisingly been found to give very good odour control and the material is easier and safer to handle the conventional "dusty" zeolites which have particles sizes up to 10 $\mu$m. Also zeolite and AGM when used together have the added advantage of being substantially white which is of importance cosmetically. In addition the odour control material used in the present invention is cheaper than some conventionally used zeolites --.

Column 4,
Line 49, after "0.7g" please insert therefor -- (about 35% by weight) --.
Line 53, after "0.4 g" please insert therefor -- (about 57% by weight) --.

Column 5,
Lines 5-12, move paragraph to line 13

Column 8,
Line 4, delete "pant liner" and insert therefor -- pantiliner --.

Signed and Sealed this

Twenty-ninth Day of June, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,096,299
DATED : August 1, 2000
INVENTOR(S) : Guarracino et al.

It is certified that error appears in the above-identified patent and that said Letters Patent is hereby corrected as shown below:

Title page,
Item [30], Foreign Application Priority Data, please delete "Feb. 23, 1995" and insert therefor -- March 25, 1994 --; please delete "TO94A0227" and insert therefor -- TO94A000227 --.
Item [57], ABSTRACT,
Line 5, please delete "um" and insert therefor -- $\mu$m --.

Column 2,
Line 21, following the heading "SUMMARY OF THE INVENTION", please insert therefor the following paragraph -- The odour control material has surprisingly been found to give very good odour control and the material is easier and safer to handle than conventional "dusty" zeolites which have particle sizes up to 10 $\mu$m. Also zeolite and AGM when used together have the added advantage of being substantially white which is of importance cosmetically. In addition the odour control material used in the present invention is cheaper than some conventionally used zeolites --.

Column 4,
Line 49, after "0.7 g" please insert therefor -- (about 35% by weight) --.
Line 53, after "0.4 g" please insert therefor -- (about 57% by weight) --.

Column 5,
Move current paragraph spanning lines 5-12 to Column 5, starting after paragraph that currently spans lines 13-18.

Column 8,
Line 4, delete "pant liner" and insert therefor -- pantiliner --.

Signed and Sealed this

Fourteenth Day of September, 2004

JON W. DUDAS
*Director of the United States Patent and Trademark Office*